(12) United States Patent
Natelson et al.

(10) Patent No.: US 8,223,330 B2
(45) Date of Patent: Jul. 17, 2012

(54) NANOSTRUCTURES AND LITHOGRAPHIC METHOD FOR PRODUCING HIGHLY SENSITIVE SUBSTRATES FOR SURFACE-ENHANCED SPECTROSCOPY

(75) Inventors: Douglas Natelson, Houston, TX (US); Daniel Robert Ward, Houston, TX (US); Zachary Kyle Keane, Houston, TX (US)

(73) Assignee: William Marsh Rice University, Houston, TX (US)

( * ) Notice: Subject to any disclaimer, the term of this patent is extended or adjusted under 35 U.S.C. 154(b) by 1192 days.

(21) Appl. No.: 12/029,631

(22) Filed: Feb. 12, 2008

(65) Prior Publication Data

US 2012/0154800 A1 Jun. 21, 2012

Related U.S. Application Data

(60) Provisional application No. 60/889,668, filed on Feb. 13, 2007.

(51) Int. Cl.
- *G01J 3/44* (2006.01)
- *B44C 1/22* (2006.01)
- *H01L 21/44* (2006.01)

(52) U.S. Cl. ........... 356/301; 216/40; 438/670; 977/881

(58) Field of Classification Search ................... 356/301; 216/40; 438/577, 670, 951; 977/880.881
See application file for complete search history.

(56) References Cited

U.S. PATENT DOCUMENTS

| | | | |
|---|---|---|---|
| 6,614,742 B2 | 9/2003 | Ueyanagi | |
| 7,857,959 B2 * | 12/2010 | Fourkas et al. | 205/118 |
| 2001/0009541 A1 | 7/2001 | Ueyanagi | |
| 2002/0153874 A1 | 10/2002 | Jiang et al. | |
| 2003/0112542 A1 | 6/2003 | Rettner et al. | |
| 2003/0198146 A1 | 10/2003 | Rottmayer et al. | |
| 2004/0211906 A1 | 10/2004 | Lendl | |
| 2005/0030993 A1 | 2/2005 | Thornton et al. | |
| 2005/0157393 A1 | 7/2005 | Hasegawa et al. | |
| 2007/0058686 A1 | 3/2007 | Capasso et al. | |

OTHER PUBLICATIONS

Park, Hongkun et al. "Fabrication of metallic electrodes with nanometer separation by electromigration". Applied Physics Letters, vol. 75, No. 2, Jul. 12, 1999, pp. 301-303.*

Alex Behfar, "Facet etching promises increased blue-laser yield" (Jul. 2005).

T. Matsumoto, T. Shimano, H. Saga and H. Sukeda, "Highly efficient probe with a wedge-shaped metallic plate for high density near-field optical recording," Journal of Applied Physics, vol. 95 No. 8, pp. 3901-3906 (Apr. 15, 2004). T. Matsumoto, Y. Anzai, T. Shintani, K. Nakamura and T. Nishida, "Writing 40 nm marks by using a beaked metallic plate near-field optical probe," Optical Letters, Vo. 31, No. 2, pp. 259-261 (Jan. 15, 2006).

T. Shintani, Y. Anzai, H. Minemura, H. Miyamoto and J. Ushiyama, "Nanosize fabrication using etching of phase-change recording films," Applied Physics Letters, vol. 85 No. 4 (Jul. 26, 2004).

* cited by examiner

*Primary Examiner* — Michael A Lyons
(74) *Attorney, Agent, or Firm* — 24IP Law Group; Timothy R. DeWitt

(57) ABSTRACT

A method for producing planar extended electrodes with nanoscale spacings that exhibit very large SERS signals, with each nanoscale gap having one well-defined hot spot. The resulting highly sensitive substrate has extended metal electrodes separated by a nanoscale gap. The electrodes act as optical antennas to enhance dramatically the local electromagnetic field for purposes of spectroscopy or nonlinear optics. SERS response is consistent with a very small number of molecules in the hotspot, showing blinking and wandering of Raman lines. Sensitivity is sufficiently high that SERS from physisorbed atmospheric contaminants may be detected after minutes of exposure to ambient conditions.

34 Claims, 8 Drawing Sheets

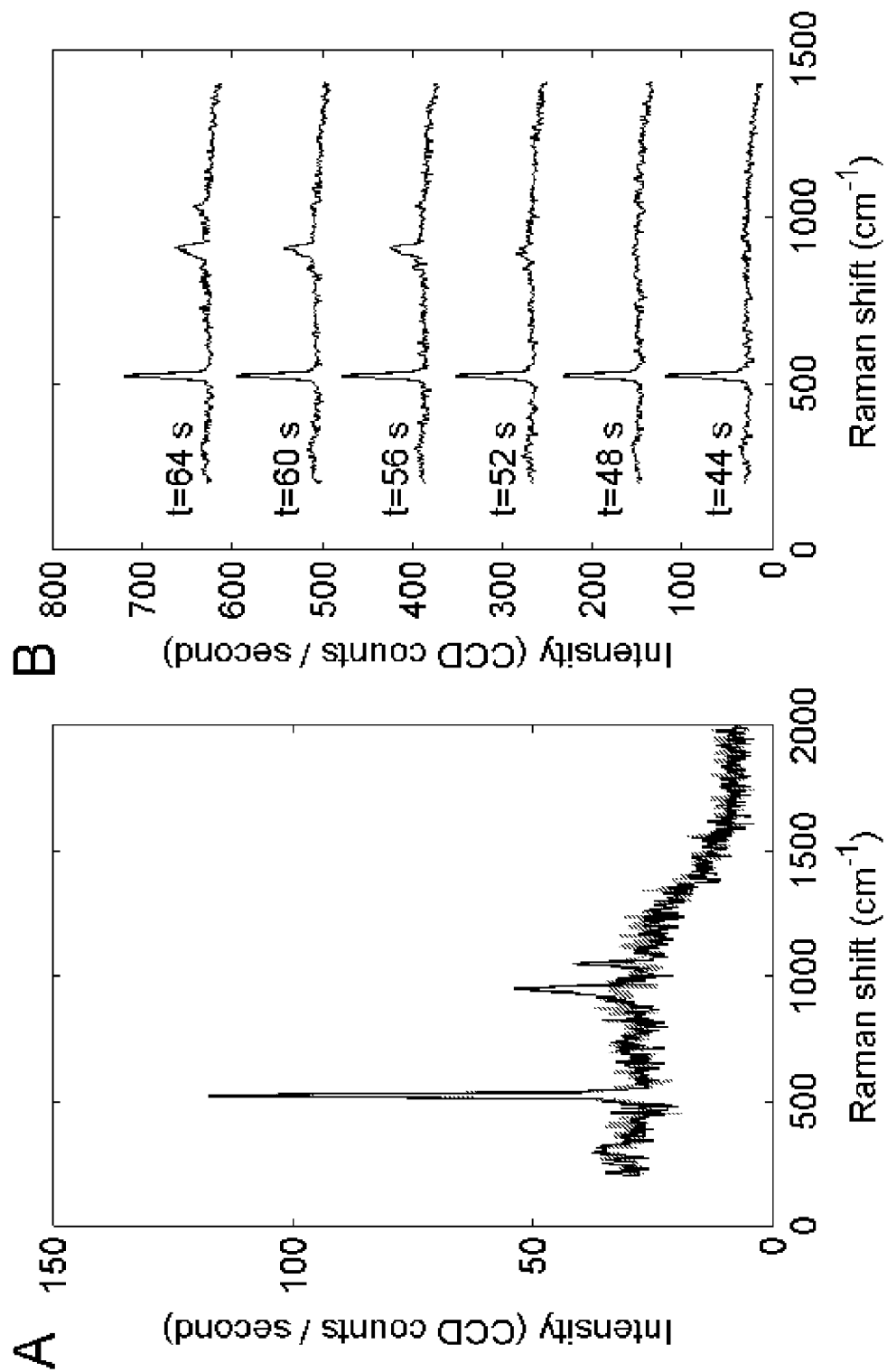
FIG. 6A-B

NANOSTRUCTURES AND LITHOGRAPHIC METHOD FOR PRODUCING HIGHLY SENSITIVE SUBSTRATES FOR SURFACE-ENHANCED SPECTROSCOPY

CROSS-REFERENCE TO RELATED APPLICATIONS

The present application claims the benefit of the filing date of U.S. Provisional Application Ser. No. 60/889,668 entitled "Lithographic Method For Producing Highly Sensitive Substrates For Surface-Enhanced Raman Spectroscopy" and filed on Feb. 13, 2007.

The above cross-referenced related application is hereby incorporated by reference herein in its entirety.

STATEMENT REGARDING FEDERALLY SPONSORED RESEARCH OR DEVELOPMENT

This invention was made with government support under National Science Foundation Grant No: DGE-0504425. The government has certain rights in the invention.

BACKGROUND OF THE INVENTION

1. Field of the Invention

The present invention relates to a new process and device design for producing substrates for highly sensitive surface-enhanced Raman spectroscopy and multimodal sensing. The resulting devices are potentially very useful for chemical sensing for a variety of applications. The large surface enhancement of electromagnetic fields may also have uses in nonlinear optics and plasmonic signal generation or routing.

2. Brief Description of the Related Art

Multifunctional sensors with single-molecule sensitivity are greatly desired for a variety of sensing applications, from biochemical analysis to explosives detection. Chemical and electromagnetic interactions between molecules and metal substrates are used in surface-enhanced spectroscopies to approach single molecule detection. See M. Moskovits, $Rev.$ $Mod.$ $Phys.$ 57, 783 (1985). Electromagnetic enhancement in nanostructured conductors results when incident light excites local electronic modes, producing large electric fields in a nanoscale region, known as a "hot spot", that greatly exceed the strength of the incident field. This local field enhancement is the mechanism responsible for a variety of "surface-enhanced" spectroscopies, including surface-enhanced Raman (SERS), surface-enhanced infrared adsorption (SEIRA), and surface-enhanced fluorescence (SEF). Hot spots can lead to particularly large enhancements of Raman scattering, since the Raman scattering rate is proportional to $|E(\omega)|^2|E(\omega')|^2$ at the location of the molecule, where $E(\omega)$ is the electric field component at the frequency of the incident radiation, and $E(\omega)$ is the component at the scattered frequency. Still, substrates that give large Raman enhancements are often useful for SEIRA and SEF as well. Large local field enhancements are also useful for nonlinear optical processes, and have been discussed in the context of optical information processing (Chang et al., $Nature$ $Physics$ 3, 807-812 (2007)).

It has been an ongoing challenge to design and fabricate a substrate for systematic surface-enhanced Raman spectroscopy (SERS) at the single molecule level. Achieving SERS with single-molecule sensitivity was first clearly demonstrated using random aggregates of colloidal nanoparticles. K. Kneipp, et al., "Colloidal silver rhodamine 6 g fluorescence spectroscopy gold," $Phys.$ $Rev.$ $Lett.$ 78, 1667 (1997); S. Nie, S. R. Emory, $Science$ 275, 1102 (1997); H. Xu, E. J. Bjerneld, M. Käll, L. Börjesson, $Phys.$ $Rev.$ $Lett.$ 83, 4357 (1999); and A. M. Michaels, J. Jiang, L. Brus, $J.$ $Phys.$ $Chem.$ $B$ 104, 11965 (2000). While numerous other metal substrate configurations have been used for SERS, including engineered nanoparticles made chemically, nanostructures defined by bottom-up patterning and traditional lithographic approaches, the most sensitive substrate geometries rely on closely adjacent subwavelength nanoparticles or nanostructures. See J. Jackson and N. J. Halas, $Proc.$ $Nat.$ $Acad.$ $Sci.$ $U.S.$ 101, 17930-17935 (2004); H. Wang, C. S. Levin and N. J. Halas, $J.$ $Am.$ $Chem.$ $Soc.$ 127, 14992-14993 (2005); C. L. Haynes, R. P. van Duyne, $J.$ $Phys.$ $Chem.$ $B$ 105, 5599 (2001); L. Qin, et al., $Proc.$ $Nat.$ $Acad.$ $Sci.$ $U.S.$ 103, 13300 (2006); D. P. Fromm, et al., $J.$ $Chem.$ $Phys.$ 124, 061101 (2006).

In this geometry, incident light may excite the collective resonance of the pair of coupled nanostructures, resulting in large field enhancements within the interparticle gap. See A. J. Hallock, P. L. Redmond, and L. E. Brus, $Proc.$ $Nat.$ $Acad.$ $Sci.$ $U.S.$ 102, 1280-1284 (2005); P. Nordlander, C. Oubre, E. Prodan, K. Li, and M. Stockman, $Nano$ $Letters$ 4, 899-903 (2004). Fractal aggregates of nanoparticles can further increase field enhancements by focusing plasmon energy from larger length scales down to particular nanometer-scale hotspots. See Z. Wang, S. Pan, T. D. Krauss, H. Du, L. J. Rothberg, $Proc.$ $Nat.$ $Acad.$ $Sci.$ $U.S.$ 100, 8638 (2003); K. Li, M. I. Stockman, D. J. Bergman, $Phys.$ $Rev.$ $Lett.$ 92, 227402 (2003). However, precise and reproducible formation of such gaps and assemblies in predetermined locations has been extremely challenging. An alternative approach is tip-enhanced Raman spectroscopy (TERS), in which the incident light excites an interelectrode plasmon resonance localized between a sharp, metal scanned probe tip and an underlying metal substrate. See D. Richards, R. G. Milner, F. Huang, F. Festy, $J.$ $Raman$ $Spectrosc.$ 34, 663 (2003); C. C. Neascu, J. Dreyer, N. Behr, M. B. Raschke, $Phys.$ $Rev.$ $B$ 73, 193406 (2006). A similar approach was recently attempted using a mechanical break junction. See J.-H. Tian, et al., $J.$ $Am.$ $Chem.$ $Soc.$ 128, 14748 (2006). While useful for surface imaging, TERS requires feedback to maintain a few-nm tip-surface gap, and is not scalable or readily integrated with other sensing modalities.

SUMMARY OF THE INVENTION

In a preferred embodiment, the present is an arrangement of pairs of planar metal electrodes fabricated on a substrate; these electrodes are separated from each other by one or more nanoscale gaps, with interelectrode separations on the few-nanometer scale; these electrodes act as nanoscale optical antennas such that, under optical illumination, the local electromagnetic field in the interelectrode gap(s) is greatly enhanced compared to the incident field. In the preferred method of the present invention, lithography is used to produce constrictions between electrode pads and then electromigration is used to break those constrictions into nanoscale gaps between the electrode pads. Using the method of the present invention, highly sensitive substrates can be produced on a mass scale using conventional industrial photolithography and wafer-probing.

With the resulting highly sensitive nanogap substrates, the Raman response is great enough to see few or even single molecules and is so sensitive that one can see atmospheric contaminants. Further, the method of the present invention fabricates SERS "hotspots" routinely, in precise locations, ready for integration with other sensing modalities (e.g. conduction, lab-on-a-chip). Each nanoscale gap may produce one hotspot. SERS emission is localized to just the nanoscale gap, not metal edges or pads. The resulting substrates have many potential uses, and may be particularly useful in sensing applications or other nonlinear optics and plasmonic applications.

In a preferred embodiment, the present invention is a method for producing highly sensitive substrates for surface-enhanced Raman spectroscopy. The method comprises the steps of lithographically defining a plurality of electrodes joined by one or several constrictions, each constriction being less that approximately 500 nm wide; depositing an electrode metal; performing liftoff after metallization; cleaning the constrictions in oxygen plasma to remove organic residue from the lithography process; performing electromigration of the constrictions until a desired interelectrode conductance is reached. The method may further comprise depositing a molecule of interest and performing Raman characterization of said molecule with a Raman microscope. The step of lithographically defining a plurality of electrodes may comprise, for example, photolithography or e-beam lithography. An alternative embodiment would be subtractive patterning: coat the desired substrate with a metal film; perform lithography to define areas of metal to be removed by subsequent etching; etch the exposed areas of metal; strip off the remaining resist and remove organic residue with oxygen plasma; then electromigrate as above. In a preferred embodiment, each electrode is hundreds of microns on a side and each constriction is approximately 100 nm wide. The step of depositing an electrode metal may comprise deposition using e-beam evaporation of 15 nm of Au with a 1 nm Ti adhesion layer.

The step of electromigration of the constrictions may be performed using a computer-controlled voltage source and current meter, may be performed until a final resistance of approximately 100 kOhms divided by the number of constrictions in parallel is reached and/or may be performed to create nanometer-scale gaps in said constrictions. The step of electromigration of the constrictions may be automated at the batch level using a standard automated probe system common to the semiconductor industry. A substrate with an array of such constrictions may be used as a master for other fabrication techniques such as imprint lithography or microcontact printing. Depending on the details of reproduction method electromigration may not be required for copies so produced.

In the preferred embodiment, the step of performing Raman characterization is performed using a WiTek scanning Raman system. Other light gathering methods are possible, including integrated local lenses and optical fibers. The method may further comprise the step of wiring up the electrodes using a wire-bonder.

In another embodiment, the present invention is a highly sensitive substrate. The highly sensitive substrate comprises a pair of planar extended metal electrodes fabricated on a substrate, said pair of electrodes being separated by a nanoscale gap with an interelectrode separation on a scale of few nanometers. The nanoscale gaps exhibit very large SERS signals, with each nanoscale gap having one well-defined hot spot. In another embodiment, the highly sensitive substrate comprises a plurality of the pairs of planar extended metal electrodes. The pair of planar extended metal electrodes may form a nanoscale optical antenna and under optical illumination an electromagnetic field in the nanoscale gap separating the pair of electrodes is greatly enhanced compared to an incident field.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which:

FIG. 6A is a Raman spectra for clean bowtie (blue) and clean bowtie after a few minutes exposed to the air (green). This change in the Raman spectrum is indicative of contamination for surface absorbed molecules from the air.

FIG. 6B is a Raman spectra for a clean bowtie showing the onset of a contaminant signal at 900 cm−1 as time progresses.

DETAILED DESCRIPTION OF THE PREFERRED EMBODIMENTS

The present invention demonstrates that planar, extended metal electrodes separated by a nanoscale gap act as optical antennas to enhance dramatically the local electromagnetic field for purposes of spectroscopy or nonlinear optics. The present invention also provides a scaleable and highly reliable method for producing planar extended electrodes with nanoscale spacings that exhibit very large SERS signals, with each nanoscale gap having one well-defined hot spot. Confocal scanning Raman microscopy demonstrates the localization of the enhanced Raman emission. SERS response is consistent with a very small number of molecules in the hotspot, showing blinking and wandering of Raman lines. Sensitivity is sufficiently high that SERS from physisorbed atmospheric contaminants may be detected after minutes of exposure to ambient conditions. The Raman enhancement for p-mercaptoaniline (pMA) is estimated from experimental data to exceed $10^9$. Finite-difference time-domain (FDTD) modeling of realistic structures reveals a rich collection of interelectrode plasmon modes that can readily lead to SERS enhancements as large as $5 \times 10^{10}$ over a broad range of illumination wavelengths. These structures hold the promise of integration of single molecule SERS with electronic transport measurements, as well as other near-field optical devices.

Figure 1:
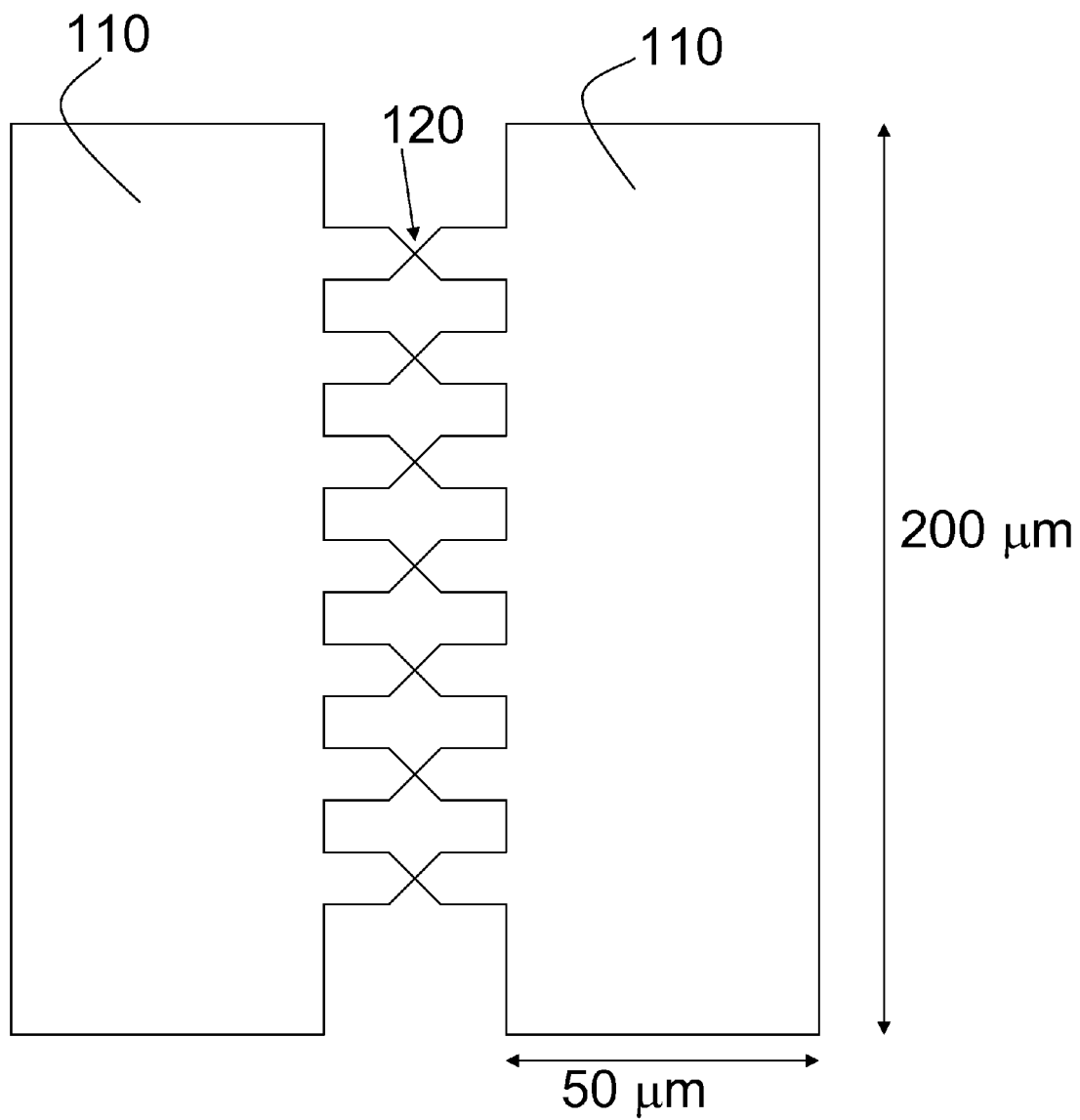
FIG. 1 is a diagram of a full multibowtie structure with seven nanoconstrictions in accordance with a preferred embodiment of the present invention.

Structures in accordance with a preferred embodiment of the present invention are fabricated on a Si wafer topped by 200 nm of thermal oxide. Electron beam lithography is used to pattern "multi-bowtie" structures as shown in FIG. 1. The multi-bowties comprise lithographically defined electrode pads 110 fabricated on an insulating substrate (not shown). The pads, for example, may be made by electron-beam lithograph and deposition of 1 nm Ti+15 Au. These materials, numbers and dimensions, however, are merely exemplary and are not critical to the present invention. Other substrates, metals, and dimensions likely could result in essentially similar functionality.

The electrode pads 110 are connected by multiple constrictions 120, as shown. The constriction widths $L_1$ in a preferred embodiment may be approximately 80-100 nm, readily within the reach of modern photolithography. This preferred width is not critical to the invention. Narrower widths would make the electromigration process easier. The length $L_2$ (shown in FIG. 2) between the electrode pads 110 is not critical to the invention. For example, the method of the present invention has experimented with lengths $L_2$ of 500 nm to 50 nm. For the electromigration, the electrical resistance between the electrode pads 110 preferably is dominated by the constriction region 120. Similarly, the precise angles and geometry of the electrode pads 110 shown in FIGS. 2A-C may vary provided that the electrodes are "extended." In other words, the electrodes preferably are much larger in extent than the wavelength of the incident radiation. Similarly, the number and arrangement of constrictions on one electrode set may vary.

Figure 2A:
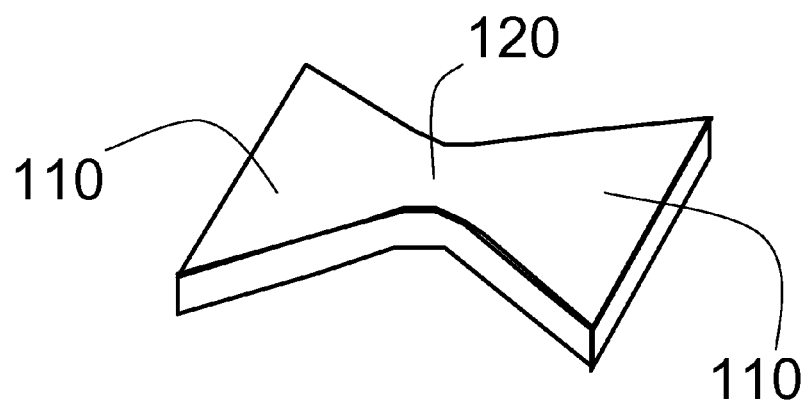
FIG. 2A is a perspective view of an individual nanoconstriction of a bowtie structure in accordance with a preferred embodiment of the present invention.
Figure 2B:
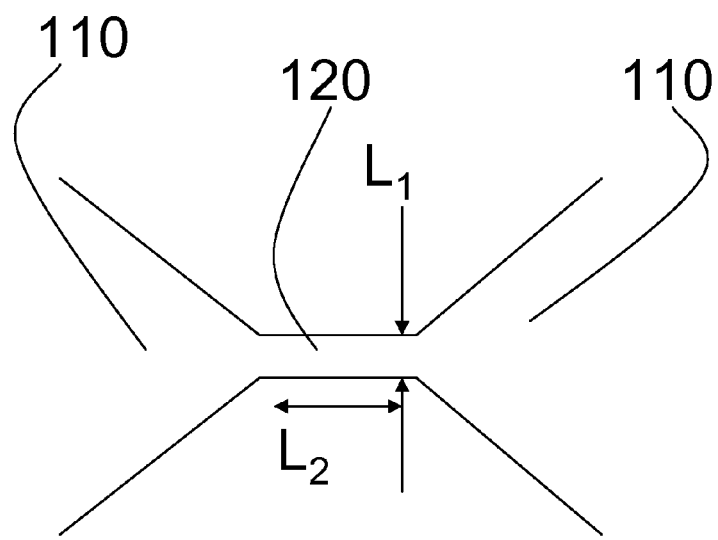
FIG. 2B is a diagram of an individual nanoconstriction of a bowtie structure in accordance with a preferred embodiment of the present invention.
Figure 2C:
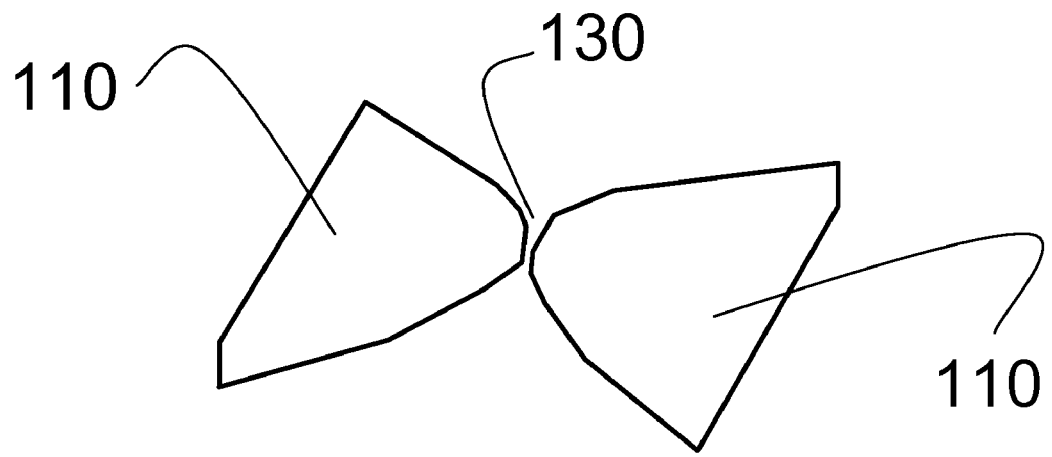
FIG. 2C is a diagram of an individual nanogap of a bowtie structure in accordance with a preferred embodiment of the present invention.

After evaporation of 1 nm Ti/15 nm Au followed by liftoff in acetone, the electrode sets are cleaned of organic residue by exposure to $O_2$ plasma for 1 minute. The multi-bowties, which comprise a plurality of individual bowties such as shown in FIGS. 2A and B, are placed in a vacuum probe station, and electromigration is used to form nanometer-scale gaps 130 in the constrictions, as shown in FIG. 2C. See H. Park, A. K. L. Lim, A. P. Alivisatos, J. Park, P. L. McEuen, *Appl. Phys. Lett.* 75, 301 (1999). Manual or automated electromigration may be performed at room temperature. In situ electromigration in the Raman measurement apparatus has also been demonstrated. The number of parallel constrictions in a single multi-bowtie is limited by the output current capacity of the electromigration voltage source. A post-migration resistance of ~10 kΩ for the structure in FIG. 1 is preferred.

Post-migration high resolution scanning electron microscopy (SEM) shows interelectrode gaps ranging from too small to resolve to several nanometers. There are no detectable nanoparticles in the gap region or along the electrode edges. Based on electromigration of 283 multibowties (1981 individual constrictions), 76.8% of multibowties have final resistances less than 100 k, and 43% have final resistances less than 25 kΩ. This yield, already high, can be improved with better process control, particularly of the lithography and liftoff. The resulting device geometries may be realizable through other fabrication methods, such as subtractive patterning, or masked/angled deposition, rather than additive patterning and electromigration as in the preferred embodiment.

In the demonstrated embodiment, the optical properties of the resulting nanogaps are characterized using a WITec CRM 200 scanning confocal Raman microscope in reflection mode, with normal illumination from a 785 nm diode laser. Using a 100× objective the resulting diffraction-limited spot is measured to be Gaussian with a full-width at half-maximum of 553 nm. The Au electrodes are clearly resolved. Rayleigh scattered light from these structures shows significant changes upon polarization rotation, while SERS response is approximately independent of polarization.

Freshly cleaned nanogaps show no Stokes-shifted Raman emission out to 3000 $cm^{-1}$. However, in 65% of clean nanogaps examined, a broad continuum background is seen, decaying roughly linearly in wavenumber out to 1000 $cm^{-1}$ before falling below detectability. This background is spatially localized to a diffraction-limited region around the interelectrode gap, and is entirely absent in unmigrated junctions. The origin of this continuum, similar to that seen in other strongly enhancing SERS substrates such as that disclosed in A. M. Michaels, J. Jiang, L. Brus, *J. Phys. Chem. B* 104, 11965 (2000), is likely inelastic electronic effects in the gold electrodes. See M. R. Beversluis, A. Bouhelier, L. Novotny, *Phys. Rev. B* 68, 115433 (2003). In samples coated with molecules, this background correlates strongly with visibility of SERS. Junctions without this background never show SERS signals. Like the SERS, this background is approximately polarization independent. Temporal fluctuations of this background in clean junctions are minimal, strongly implying that fluctuations of the electrode geometry are not responsible for SERS blinking.

The SERS enhancement of the junctions has been tested using various molecules. The bulk of testing employing paramercaptoaniline (pMA), which self-assembles onto the Au electrodes via standard thiol chemistry. Particular modes of interest are carbon ring modes at 1077 $cm^{-1}$ and 1590 $cm^{-1}$. The emission is strongly localized to the position of the nanogap. No Raman signal is detectable either on the metal films or at the edges of the metal electrodes.

Figure 3:
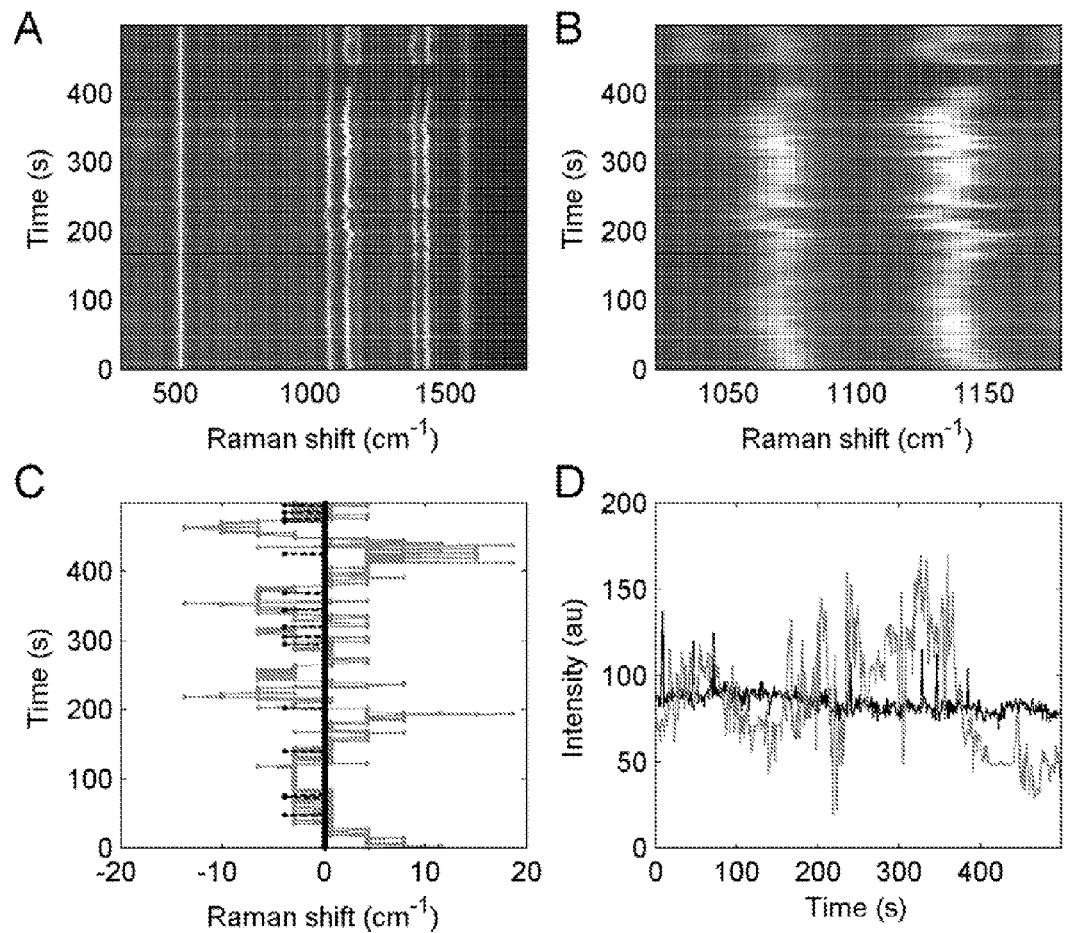
FIGS. 3A-D show an examination of the SERS response of the gap region of a typical junction after self-assembly of para-mercaptoaniline (pMA), a diagnostic molecule used in accordance with a preferred embodiment of the present invention

FIG. 3 shows an examination of the SERS response of the gap region of a typical junction after self-assembly of pMA. FIGS. 3A and B are time series of the SERS response, with known pMA modes indicated. The modes visible are similar to those seen in other SERS measurements of pMA on lithographically fabricated Au structures. See D. P. Fromm, et al., *J. Chem. Phys.* 124, 061101 (2006). Each spectrum was acquired with 1 integration time, with the microscope positioned over the center of the nanogap hotspot. Temporal fluctuations of both the Raman intensity ("blinking") and Raman shift ("wandering"), generally regarded as hallmarks of few- or single-molecule SERS sensitivity (see Z. Wang, L. J. Rothberg, *J. Phys. Chem. B* 109, 3387 (2005)), are readily apparent. FIG. 3C shows a comparison of the wandering of the 1077 cm−1 pMA line with that of the 520 $cm^{-1}$ Raman line of the underlying Si substrate over the same time interval. This demonstrates that the wandering is due to changes in the molecular environment, rather than a variation in spectrometer response. FIG. 3D shows the variation in the peak amplitudes over that same time interval.

This blinking and wandering is seen routinely in these junctions. Such Raman response has been observed from several molecules, including self-assembled films of pMA, p-mercaptobenzoic acid (pMBA), a Co-containing transitionmetal complex (see J. Ciszek, et al., *J. Am. Chem. Soc.* 128, 3179 (2006)), and spin-coated poly(3-hexylthiophene)

(P3HT). These molecules have distinct Raman responses and all show blinking and wandering in the junction hotspots.

Another indicator of very large enhancement factors in these structures is sensitivity to exogenous, physisorbed contamination. Carbon contamination has been discussed in the context of both SERS and TERS. D. Richards, R. G. Milner, F. Huang, F. Festy, *J. Raman Spectrosc.* 34, 663 (2003); A. Otto, *J. Raman Spectrosc.* 33, 593 (2002). This substrate is sensitive enough to examine the arrival of such contaminants. Clean nanospaced junctions with no deliberately attached molecules initially show no Raman features beyond the continuum background mentioned above. However, after exposure to ambient lab conditions for tens of minutes, SERS signatures in the sp$^2$ carbon region between 1000 cm$^{-1}$ and 1600 cm$^{-1}$ are readily detected, localized to the interelectrode gap, like all SERS signatures on these substrates. Interestingly, nanojunctions that have been coated with a self-assembled monolayer (SAM) (for example, pMA) do not show this carbon signature, even after hours of ambient exposure. Presumably this has to do with the extremely localized field enhancement in these structures, with the SAM sterically preventing physisorbed contaminants from entering the region of enhanced near field.

Recently arrived contaminant SERS signatures disappear in tens of seconds at high laser intensities (26 kW/cm$^2$), presumably due to desorption. SERS from covalently bound molecules is considerably more robust, persisting for hours for intensities below 10.4 kW/cm$^2$. SEM examination of the nanogaps shows no obvious signs of optically induced damage or melting after exposure to intensities that would significantly degrade nanoparticles. See P. Schuck, D. Fromm, A. Sundaramurthy, G. Kino, W. Moerner, *Phys. Rev. Lett.* 94, 017402 (2005). The large extended pads likely aid in the thermal sinking of the nanogap region to the substrate.

Figure 4:
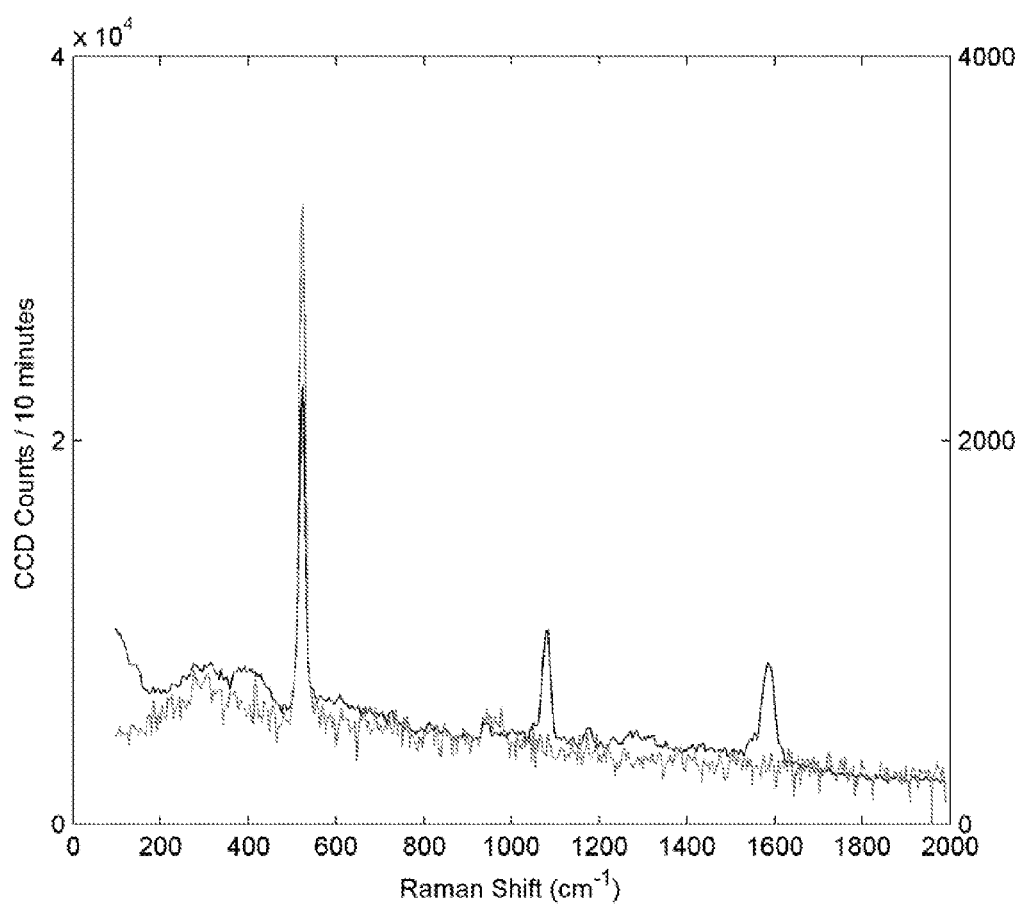
FIG. 4 shows a comparison between a typical pMA SERS spectrum acquired on a junction with a 600 second integration time at 10.4 kW/cm$^2$ incident intensity, and a spectrum acquired over one of that device's Au pads, for the same settings.

Estimating enhancement factors rigorously is notoriously difficult, particularly when the hotspot size is not known. Although SERS enhancement volume measurements are feasible using molecular rulers, such an approach is not feasible with such small nanogaps. See S. Lal, N. K. Grady, G. P. Goodrich and N. J. Halas, *Nano Letters* 6, 2338-2343 (2006). Fabrication of nanogaps directly on Raman-active substrates allows some estimation of the enhanced volume in the direction normal to the substrate. Junctions fabricated directly on Raman-active substrates (Si with no oxide; GaAs) show essentially no clearly detectable enhancement of the substrate Raman response in the gap region. This suggests that the region of electromagnetic enhancement is strongly confined to the thickness of the metal film electrodes. FIG. 4 shows a comparison between a typical pMA SERS spectrum acquired on a junction with a 600 second integration time at 10.4 kW/cm$^2$ incident intensity, and a spectrum acquired over one of that device's Au pads, for the same settings. The pad spectrum shows no detectable pMA features and is dark current limited.

FDTD calculations were used to understand the strong SERS response in these structures and estimate the enhancement factors theoretically. These calculations also allow an estimate of the hotspot volume, so that the data in FIG. 4 may be used to arrive at an experimental bound on the enhancement.

Figure 5:
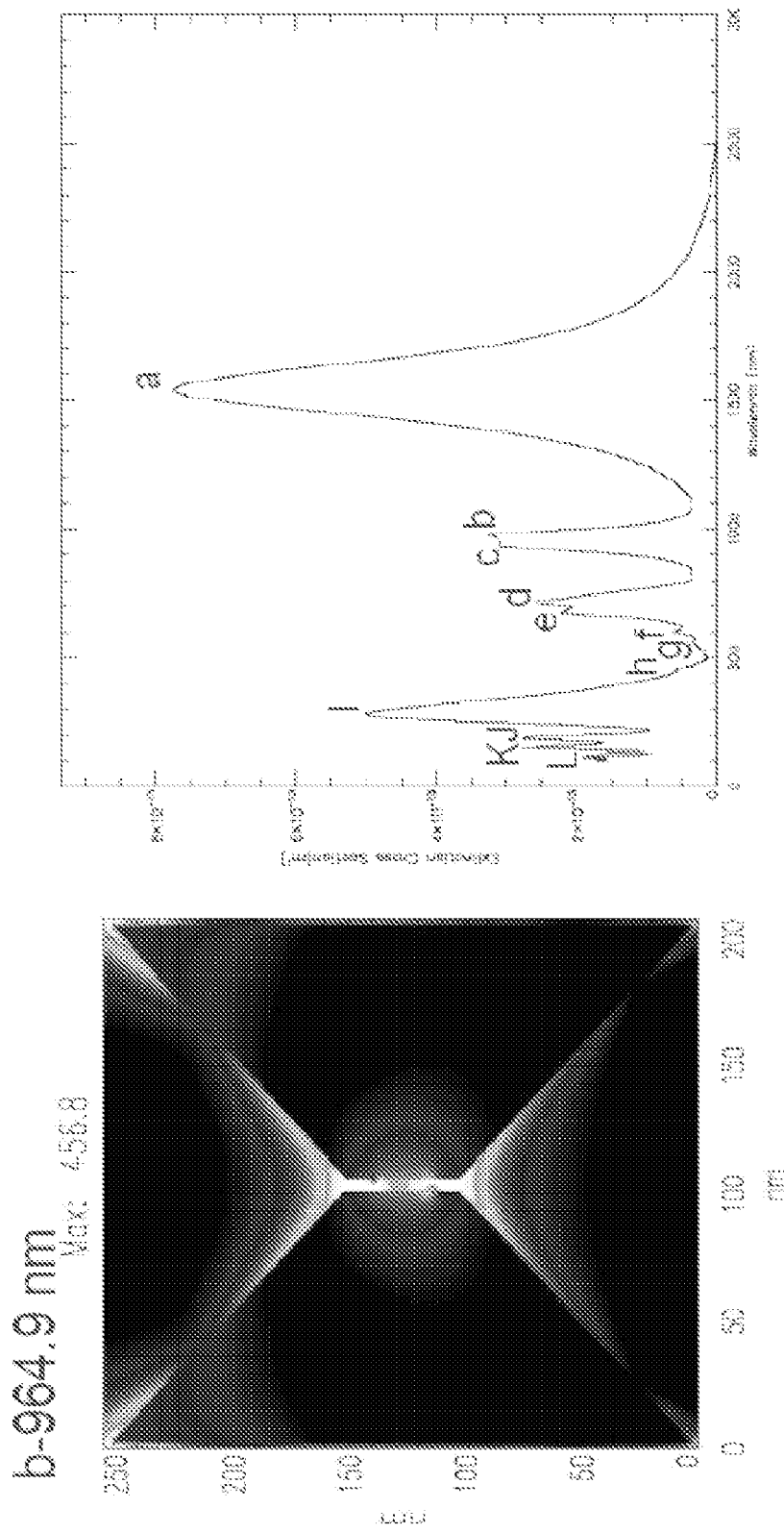
FIG. 5 shows a calculated map of the field enhancement in the vicinity of the junction in a device in accordance with a preferred embodiment of the present invention.

FIG. 5 shows a calculated map of the field enhancement in the vicinity of the junction. These calculations do not account for reduced carrier mean free path due to surface scattering in the metal film, nor do they include interelectrode tunneling. However, such effects are unlikely to change the results significantly.

These calculations predict that there should be large SERS enhancements across a broad bandwidth of exciting wavelengths because of the complicated mode structure possible in the interelectrode gap. Nanometer-scale asperities from the electromigration process break the interelectrode symmetry of the structure. The result is that optical excitations at a variety of polarizations can excite many interelectrode modes besides the simple dipolar plasmon commonly considered. This broken symmetry also leads to much less dependence of the calculated intensity on polarization direction, as seen experimentally. The calculations confirm that the field enhancement is confined in the normal direction to the film thickness. Laterally, the field enhancement is confined to a region comparable to the radius of curvature of the asperity. These calculations predict a purely electromagnetic enhancement that can approach $10^{11}$, approaching that sufficient for single-molecule sensitivity.

Using the calculated effective hotspot area and data from the device in FIG. 4, we estimate the total enhancement in that device. Assuming a hotspot effective radius of 2.5 nm, consistent with the FDTD calculations, the number of molecules in the hotspot is approximately N≈100, assuming the known pMA packing density. The integrated Raman signal, S, over the band from 1000 cm$^{-1}$ to 1700 cm$^{-1}$ after background subtraction is 218 counts/sec when the incident intensity is 10.4 kW/cm$^2$=4.1×10$^{22}$ photons/s/cm$^2$ at 785 nm. Using a Raman cross-section σ~10$^{-29}$ cm$^2$, a detector collection efficiency of 0.04 photons/s cm$^{-2}$ (including the efficiency of the spectrometer CCD), we estimate a total enhancement of at least 1.3×10$^9$.

The present invention provides a SERS substrate capable of extremely high sensitivity for trace chemical detection. Unlike previous substrates, these nanojunctions may be mass fabricated in controlled positions with high yield using a combination of standard lithography and electromigration. The resulting hotspot geometry is predicted to allow large SERS enhancements over a broad band of illuminating wavelengths. Other nonlinear optical effects should be observable in these structures as well. The extended electrode geometry and underlying gate electrode are ideal for integration with other sensing modalities such as electronic transport. Tuning molecule/electrode charge transfer via the gate electrode may also enable the direct examination of the fundamental nature of chemical enhancement in SERS.

Figure 6C:
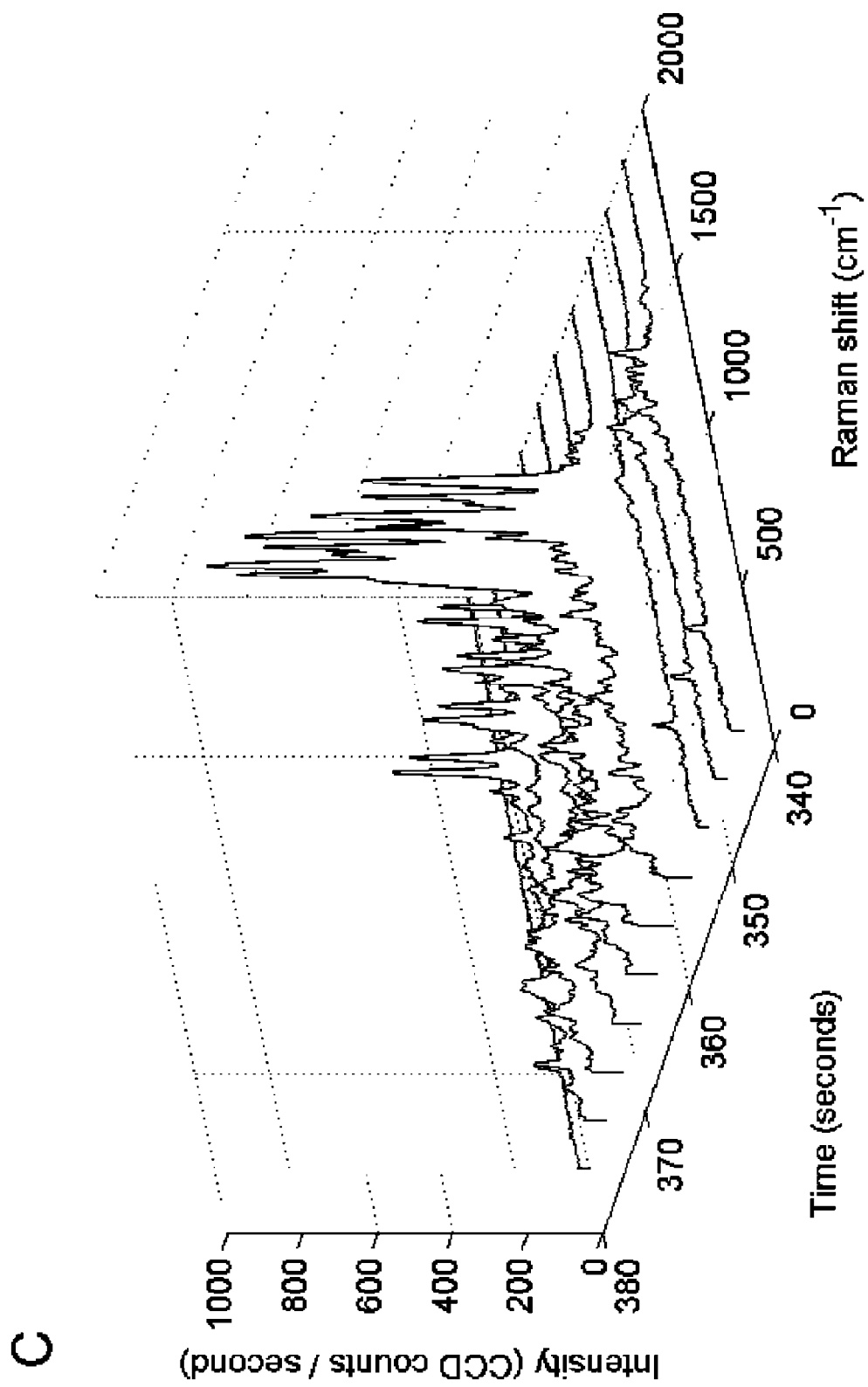
FIG. 6C is a waterfall plot showing the extremely strong blinking observed for adsorbed contamination. The fluctuations are much larger than those observed for dense coverage of pMA, pMBA, or P3HT. Notice the scale relative to the 520 cm−1 Si peak seen at t=340 s.

Due to the large enhancements possible with the nanogaps, contamination from airborne absorbates occurs readily in the absence of assembled molecules on the nanogap surface. We have observed the absorption of contaminates onto the surface of clean nanogaps in as little as 10 minutes. Collecting Raman spectra every 4 seconds, we can observe the appearance of contaminants on the surface as seen in FIGS. 6A and 6B. It is difficult to identify the contaminants, as the spectra observed have large variations, although carbon ring modes are often observed in conjunction with other modes. Furthermore the Raman signal from contaminants often blinks very strongly, with periods of no or weak signal followed by several seconds of intense blinking, as seen in FIG. 6C. The changes in intensity can be more than a factor of 100. Again we suggest that the strong blinking is a result of the weak attachment of the contaminates to the nanogap surface, allowing them to move considerably and explore many interactions with the Au surface. As previously mentioned, these contamination spectra are not observed when molecules of interest have been preassembled deliberately on the electrode surface. The likely explanation for this is that the molecules of interest sterically prevent contaminants from arriving at the nanogap region of maximum field enhancement.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for producing a plurality of highly sensitive substrates, the method comprising the steps of:
   lithographically defining a plurality of electrodes joined by one or several constrictions, each constriction being less than 500 nm wide;
   depositing an electrode metal;
   performing liftoff after metallization;
   cleaning said constrictions in oxygen plasma to remove organic residue from the lithography process; and
   performing electromigration of the constrictions until a desired interelectrode conductance is reached.

2. A method for producing a plurality of highly sensitive substrates in accordance with claim 1 wherein said step of lithographically defining a plurality of electrodes comprises photolithography.

3. A method for producing a plurality of highly sensitive substrates in accordance with claim 1, further comprising the step of depositing a molecule of interest.

4. A method for producing a plurality of highly sensitive substrates in accordance with claim 3, further comprising the step of performing characterization of said molecule.

5. A method for producing a plurality of highly sensitive substrates in accordance with claim 3, further comprising the step of performing Raman characterization of said molecule with a Raman microscope.

6. A method for producing a plurality of highly sensitive substrates in accordance with claim 1 wherein said step of lithographically defining a plurality of electrodes comprises e-beam lithography.

7. A method for producing highly sensitive substrates in accordance with claim 1 wherein each electrode defined in said step of lithographically defining a plurality of electrodes is hundreds of microns on a side.

8. A method for producing a plurality of highly sensitive substrates in accordance with claim 1 wherein each of said constrictions is approximately 100 nm wide.

9. A method for producing a plurality of highly sensitive substrates in accordance with claim 1 wherein said step of depositing an electrode metal comprises deposition using e-beam evaporation of 15 nm of Au with a 1 nm Ti adhesion layer.

10. A method for producing a plurality of highly sensitive substrates in accordance with claim 1 wherein said step of electromigration of the constrictions is performed using a computer-controlled voltage source and current meter.

11. A method for producing a plurality of highly sensitive substrates in accordance with claim 1 wherein said step of electromigration of the constrictions is performed until a final resistance of approximately 100 kOhms divided by the number of constrictions in parallel is reached.

12. A method for producing a plurality of highly sensitive substrates in accordance with claim 1 wherein said step of electromigration of the constrictions is performed to create nanometer-scale gaps in said constrictions.

13. A method for producing a plurality of highly sensitive substrates in accordance with claim 1 wherein said step of electromigration of the constrictions is automated at the batch level using a standard automated probe system common to the semiconductor industry.

14. A method for producing a plurality of highly sensitive substrates in accordance with claim 1 wherein said step of performing Raman characterization is performed using a WiTek scanning Raman system.

15. A method for producing a plurality of highly sensitive substrates in accordance with claim 1 further comprising the step of wiring up the electrodes using a wire-bonder.

16. A method for producing a plurality of highly sensitive substrates comprising the steps of:
   depositing an electrode metal;
   lithographically defining a plurality of electrodes joined by one or several constrictions, each less than approximately 500 nm wide;
   subtractive patterning of the electrode metal by etching;
   removal of remaining resist;
   cleaning said constrictions in oxygen plasma to remove organic residue from the lithography process;
   and performing electromigration of the constrictions until a desired interelectrode conductance is reached.

17. A method for producing a plurality of highly sensitive substrates in accordance with claim 16, further comprising the step of depositing a molecule of interest.

18. A method for producing a plurality of highly sensitive substrates in accordance with claim 17, further comprising the step of performing characterization of said molecule.

19. A method for producing a plurality of highly sensitive substrates in accordance with claim 17, further comprising the step of performing Raman characterization of said molecule with a Raman microscope.

20. A method for producing a plurality of highly sensitive substrates in accordance with claim 16 wherein said step of lithographically defining a plurality of electrodes comprises e-beam lithography.

21. A method for producing highly sensitive substrates in accordance with claim 16 wherein each electrode defined in said step of lithographically defining a plurality of electrodes is hundreds of microns on a side.

22. A method for producing a plurality of highly sensitive substrates in accordance with claim 16 wherein each of said constrictions is approximately 100 nm wide.

23. A method for producing a plurality of highly sensitive substrates in accordance with claim 16 wherein said step of depositing an electrode metal comprises deposition using e-beam evaporation of 15 nm of Au with a 1 nm Ti adhesion layer.

24. A method for producing a plurality of highly sensitive substrates in accordance with claim 16 wherein said step of electromigration of the constrictions is performed using a computer-controlled voltage source and current meter.

25. A method for producing a plurality of highly sensitive substrates in accordance with claim 16 wherein said step of electromigration of the constrictions is performed until a final resistance of approximately 100 kOhms divided by the number of constrictions in parallel is reached.

26. A method for producing a plurality of highly sensitive substrates in accordance with claim 16 wherein said step of electromigration of the constrictions is performed to create nanometer-scale gaps in said constrictions.

27. A method for producing a plurality of highly sensitive substrates in accordance with claim 16 wherein said step of electromigration of the constrictions is automated at the batch level using a standard automated probe system common to the semiconductor industry.

28. A method for producing a plurality of highly sensitive substrates in accordance with claim 16 wherein said step of performing Raman characterization is performed using a WiTek scanning Raman system.

29. A method for producing a plurality of highly sensitive substrates in accordance with claim 16 further comprising the step of wiring up the electrodes using a wire-bonder.

30. A method for performing surface enhanced Raman spectroscopy on a molecule of interest, the method comprising the steps of:
 lithographically defining a plurality of electrodes joined by several constrictions, each approximately 100 nm wide;
 depositing an electrode metal;
 performing liftoff after metallization;
 cleaning said constrictions in oxygen plasma to remove organic residue from the lithography process;
 performing electromigration of the constrictions until a desired interelectrode conductance is reached;
 depositing a molecule of interest; and
 performing Raman characterization of said molecule with a Raman microscope.

31. A method for performing simultaneous surface enhanced Raman spectroscopy and electronic conduction measurements on a molecule of interest, the method comprising the steps of:
 lithographically defining a plurality of electrodes joined by one or several constrictions, each approximately 100 nm wide;
 depositing an electrode metal;
 performing liftoff after metallization;
 cleaning said constrictions in oxygen plasma to remove organic residue from the lithography process;
 performing electromigration of the constrictions until a desired interelectrode conductance is reached;
 depositing a molecule of interest; performing Raman characterization of said molecule with a Raman microscope; and
 simultaneously using the electrodes to measure the electronic conduction across the interelectrode gap.

32. A highly sensitive substrate comprising:
 a pair of planar extended metal electrodes fabricated on a substrate, said pair of electrodes being separated by a nanoscale gap with an interelectrode separation on a scale of few nanometers;
 wherein said nanoscale gaps exhibit very large surface-enhanced Raman signals, with each nanoscale gap having one well-defined hot spot.

33. A highly sensitive substrate according to claim 32, further comprising a plurality of said pairs of planar extended metal electrodes.

34. A highly sensitive substrate according to claim 32 wherein said pair of planar extended metal electrodes form a nanoscale optical antenna and under optical illumination, an electromagnetic field in said nanoscale gap separating said pair of electrodes is greatly enhanced compared to an incident field.

* * * * *